United States Patent [19]

Cancio et al.

[11] Patent Number: 5,084,039
[45] Date of Patent: Jan. 28, 1992

[54] DISPOSABLE DIAPERS, ABSORBENT ARTICLES AND THERMOPLASTIC SHEET MATERIAL HAVING IMPROVING TAPE ADHESION

[75] Inventors: Leopoldo V. Cancio, Cincinnati, Ohio; Thomas R. Ryle, Burlington, Ky.; Robert J. Tomany, Fairfield; Pai-Chuan Wu, Cincinnati, both of Ohio

[73] Assignee: Clopay Corporation, Cincinnati, Ohio

[21] Appl. No.: 363,296

[22] Filed: Jun. 7, 1989

Related U.S. Application Data

[63] Continuation of Ser. No. 32,004, Mar. 27, 1987, abandoned.

[51] Int. Cl.$^5$ .............................................. A61F 13/15
[52] U.S. Cl. .................................... 604/366; 604/389; 525/209
[58] Field of Search ............... 604/366, 370, 384, 389, 604/390; 525/209, 232, 240

[56] References Cited

U.S. PATENT DOCUMENTS

| | | | |
|---|---|---|---|
| 3,426,754 | 2/1969 | Bierenbaum et al. | 604/370 |
| 3,840,418 | 10/1974 | Sabee | 604/366 |
| 3,843,478 | 10/1974 | Zuscik | 604/370 |
| 4,166,464 | 9/1979 | Korpman | 604/372 |
| 4,436,520 | 3/1984 | Lipko et al. | 604/389 |
| 4,525,577 | 7/1985 | Schmidt, Jr. et al. | 604/366 |
| 4,540,415 | 9/1985 | Korpman | 604/389 |
| 4,542,188 | 9/1985 | van der Heijden | 525/240 |
| 4,624,991 | 11/1986 | Haas | 525/209 |
| 4,626,252 | 12/1986 | Nishizawa et al. | 604/370 |
| 4,655,761 | 4/1987 | Grube et al. | 604/390 |
| 4,657,802 | 4/1987 | Morman | 604/358 |
| 4,710,186 | 12/1987 | De Rossett et al. | 604/383 |
| 4,713,068 | 12/1987 | Wang et al. | 604/378 |

FOREIGN PATENT DOCUMENTS

| | | | |
|---|---|---|---|
| 0012033 | 6/1980 | European Pat. Off. | 604/366 |
| 0041342 | 3/1984 | Japan . | |
| 0202244 | 11/1984 | Japan | 525/240 |

Primary Examiner—C. Fred Rosenbaum
Assistant Examiner—Sharon Finkel
Attorney, Agent, or Firm—Wood, Herron & Evans

[57] ABSTRACT

Novel thermoplastic sheet materials for permitting positionable and repeated repositionable use of tape fasteners therewith without experiencing substnatial loss of tape adhesion therebetween are disclosed. A novel thermoplastic sheet material generally comprises an ethylene polymer and an anti-popoff polymer in an effective amount for increasing and substantially maintaining the tape adhesion. The increase in and substantial maintenance of the tape adhesion is accomplished without adversely affecting the properties or cost of the thermoplastic sheet material. A preferred formulation for producing the novel thermoplastic sheet material comprises polyethylene as the ethylene polymer and a polypropylene or alpha-methyl styrene as the anti-popoff polymer. The novel thermoplastic sheet materials are especially suitable for use as films which can be used as backsheets in absorbent articles, such as, disposable diapers, bandages, surgical dressings or drapes and catamenial pads.

62 Claims, 2 Drawing Sheets

DISPOSABLE DIAPERS, ABSORBENT ARTICLES AND THERMOPLASTIC SHEET MATERIAL HAVING IMPROVING TAPE ADHESION

This application is a continuation of application Ser. No. 032004, filed Mar. 27, 1987, now abandoned.

FIELD OF THE INVENTION

The present invention relates to a thermoplastic sheet material, and more particularly to a thermoplastic sheet material for use with absorbent articles, such as disposable diapers, wherein the thermoplastic sheet material has improved tape adhesion with pressure-sensitive adhesive tape-tabs.

BACKGROUND

It has become common practice today to use disposable diapers with infants and incontinent people. Disposable diapers generally have a rectangular or hour glass shape and comprise an absorbent batt material sandwiched between an outer flexible polyethylene backsheet and an inner flexible, polypropylene or polyester nonwoven frontsheet. The outer backsheet typically, but not necessarily, is water-impervious to prevent voided liquid absorbed into the absorbent batt material from striking through the diaper and soiling the infant's adjacent clothing or bedding. The inner frontsheet on the other hand is water-pervious to permit the voided liquid to pass therethrough into the absorbent batt material to maintain the infant in a dry, comfortable state.

It is also well known and common practice in manufacturing disposable diapers to rely upon tape-tab fasteners as means for fastening the diapers about infants. The safety advantages and practicality of tape-tabs, rather than pins, is self evident. However, there are several shortcomings associated with their use. One major shortcoming lies in the loss or lack of tape adhesion between the tape-tab fasteners and backsheets following the original closures preventing the tape-tab fasteners from being positioned or repositioned on the backsheets. This shortcoming becomes immediately apparent when users, such as nurses or parents, attempt to separate the tape-tab fasteners from the diapers to inspect for soiling and refasten them following their inspection or when the diapers fall off due to the failure of tape-tab fasteners.

Some backsheet materials available heretofore for disposable diapers have very poor tape adhesion, i.e., the pressure-sensitive adhesives of the tape-tab fasteners do not or cannot adhere to the backsheets, making positioning or repositioning very cumbersome, if not virtually impossible. Unfortunately, this results in unsoiled diapers being discarded and wasted following routine inspection or childrens' participation in the toilet-training ritual. This lack of reusability not only is inconvenient but also expensive because of the rising costs associated with disposable diapers.

In one attempt to solve the refastening problem, U.S. Pat. No. 4,163,077, issued to Antonsen et al. on July 31, 1979, proposes to formulate the pressure-sensitive adhesive of the tape-tab fasteners with a rubbery block copolymer tackified with a combination of certain liquid and solid tackifiers to improve adhesion and shear properties when the backsheet is contaminated with foreign substances, such as talcum powder.

While U.S. Pat. No. 4,163,077 reflects one attempt, there have been other attempts made in the past to solve the repositioning problem. Unfortunately, they have attempted to solve such problem by modifying either the tape-tab fasteners, the pressure-sensitive adhesives used therewith or by coating the tape-tab fastener bonding regions located on the backsheets. These closure systems have the disadvantages of restricting the disposable diaper manufacturers to a particular tape-tab fastener arrangement, a particular pressure-sensitive adhesive formulation or added manufacturing steps, and forcing them to select only those backsheets that are coated at the bonding regions or are compatible with such arrangements or pressure-sensitive adhesive formulations in order to produce an effective repositionable closure system. Such methods also have the disadvantage of adding to the cost of manufacturing disposable diapers.

Consequently, there is a definite need for a repositionable yet inexpensive and flexible closure system that is not restricted to a particular tape-tab fastener arrangement, pressure-sensitive adhesive formulation or coated backsheet, that has good tape adhesion when the diapers are initially closed, and that does not lose substantial tape adhesion upon repeated use of the tape-tab fasteners following occasional inspection for soiling or childrens' participation in the toilet-training ritual permitting unsoiled diapers to be reused.

SUMMARY OF THE INVENTION

In brief, the present invention alleviates the above mentioned problems and shortcomings of the present state of the art through the discovery of a novel thermoplastic sheet material for permitting positionable and repeated repositionable use of a tape fastener therewith without experiencing substantial loss of tape adhesion therebetween. More particularly, the novel thermoplastic sheet material comprises an ethylene polymer and an anti-popoff substance in an effective amount which accounts for the increase in and substantial maintenance of the tape adhesion. The ethylene polymer can be a low density polyethylene, a linear low density polyethylene, a high density polyethylene or suitable blends thereof. The anti-popoff polymer can be, for instance, polypropylene, alpha-methyl styrene, ethylene-propylene copolymer and styrenic copolymers, such as styrene-butadiene-styrene block copolymer and styrene-isoprene-styrene block copolymer, which is preferably present in an amount of about greater than zero up to about ten percent by weight of the sheet material. The unique increase in and substantial maintenance of the tape adhesion associated with the thermoplastic sheet materials of this invention is accomplished without adversely affecting the properties or cost of the sheet material while obtaining the desired advantage of permitting positionable and repeated repositionable use of tape fasteners therewith. Moreover, in following the teachings of the present invention, disposable diaper manufacturers are no longer restricted to a particular tape-tab fastener arrangement or pressure-sensitive adhesive formulation since the thermoplastic sheet materials of this invention, when used as backsheets, can be formulated for compatible use with almost any repositionable tape-tab fastener or system.

The novel thermoplastic sheet materials of this invention are especially suitable for use as films which can be used as backsheets in absorbent articles, such as bandages, surgical dressings or drapes and catamenial pads, and are especially suitable for use as backsheets in disposable diapers. When the thermoplastic sheet materials of this invention are used to formulate the backsheets of disposable diapers, they uniquely afford cost saving and convenience advantages to users by permitting the tape-tab fasteners to be repositioned to the backsheets so that diapers can be reused with confidence following routine inspection or the toilet-training ritual. In other words, the refastened tape-tabs will adhere firmly to the backsheets, and the disposable diapers will remain in place following their opening or removal by the users. The present invention therefore now makes it possible to initially close a disposable diaper with confidence and to open the originally closed diaper for occasional inspection without fear that the tape-tab fasteners will not reposition on the backsheet, or without fear that the disposable diaper will reopen at some point following the original closure or a subsequent closure.

The above features and advantages of the present invention will be better understood with reference to the accompanying Figs., Detailed Description and Examples. It also should be understood that the particular thermoplastic sheet materials, absorbent articles and methods of this invention are exemplary only and not to be regarded as limitations of the invention.

BRIEF DESCRIPTION OF THE FIG.

Reference is now made to the accompanying Figs. from which the novel features and advantages of the present invention will be apparent.

DETAILED DESCRIPTION OF THE INVENTION

By way of illustrating and providing a more complete appreciation of the present invention and many of the attendant advantages thereof, the following detailed description and examples are given concerning the novel thermoplastic sheet materials, absorbent articles made therewith and methods of production and use thereof.

As used herein, the term "tape adhesion" refers broadly to the force required to remove or separate a pressure-sensitive adhesive fastener from a thermoplastic sheet material. The force required to remove or separate the fastener from the thermoplastic sheet material is generally measured at a specified angle and at a given speed. Tests to determine tape adhesion may be conducted with an one-inch width fastener, such as a pressure-sensitive adhesive tape-tab fastener, at 90° (Test method A) and 180° (Test method B) angles of peel at a pull speed of approximately 12 inches per minute at any desirable speed. Of course, it should be understood that the tape adhesion can be measured at any other angle, such as between 90° and 180° (Test method C) and at different pull speeds. The results may be expressed in grams per inch width of the tape-tab fastener or in percent increase as a function of the anti-popoff substance content.

Referring now more particularly to the present invention, the thermoplastic sheet material comprises an ethylene polymer and an anti-popoff Polymer in an effective amount for increasing and substantially maintaining the tape adhesion between the thermoplastic sheet material and a pressure-sensitive adhesive fastener adhered thereto. In other words, the uniquely formulated thermoplastic sheet materials provide for improved tape adhesion following the original or subsequent bonding of a tape fastener to the thermoplastic sheet material. The ethylene polymers which may be used to formulate the thermoplastic sheet materials of the present invention can be homopolymers of ethylene made from ethylene monomers or comonomers of ethylene with, for example, butene, hexene, octene and methyl pentene. Particular ethylene polymers that are suitable for use in the present invention are polyethylenes and more particularly low, linear low or high density polyethylenes or any suitable blends thereof.

By the term "anti-popoff polymer," it is meant herein to refer broadly to any Polymer that, when combined with an ethylene polymer to form a thermoplastic sheet material of the present invention, can act to increase and substantially maintain the tape adhesion between the thermoplastic sheet material and a pressure-sensitive adhesive fastener for permitting positionable and repeated repositionable use of the fastener therewith. The unique formulation of an anti-popoff polymer in an effective amount with an ethylene polymer can be used to formulate a novel thermoplastic sheet material of the present invention which is believed to be more resistant to tape fastener peel following positioning or repositioning than heretofore achieved. In other words, the thermoplastic sheet materials of the present invention prevents pressure-sensitive adhesive fasteners from popping off of the sheet materials following their being initially positioned or repositioned thereon.

In determining how much of the anti-popoff Polymer to incorporate into the thermoplastic sheet material, it is necessary to take into account the pressure-sensitive adhesive of the tape fastener selected for use. When anti-popoff polymers having high bonding affinities for the pressure-sensitive adhesives are selected, lesser amounts are required to be incorporated into the sheet materials than when anti-popoff polymers having low bonding affinities are selected. Nevertheless, it is found as a general rule that an effective amount can range from about greater than 0 up to about 10% and more particularly from about 0.75% to about 5% by weight of the thermoplastic sheet material. Regardless of the amount utilized, however, it is preferred to utilize an amount that does not cause the tape adhesion to exceed the tearing strength of the sheet material which can be determined by any conventional technique well known to those versed in the art. The tearing strength is a function of, inter alia, the thickness and components of the thermoplastic sheet materials. Preferred anti-popoff polymers which may be used to formulate the thermoplastic sheet materials of the present invention are polyproylenes and copolymers thereof, alpha-methyl styrene and styrenic copolymers. The preferred anti-popoff polymers include polypropylene, alpha-methyl styrene, ethylene-propylene copolymer, styrenic copolymers, such as styrene-butadiene-styrene block copolymer and styrene-isoprene-styrene block copolymer, and suitable mixtures thereof. The most preferred anti-popoff polymers are a polypropylene and an alpha-methyl styrene. Although the above represents preferred amounts and anti-popoff polymers, it should be understood that any effective amount of and any suitable substance, polymer or blends of polymers may be used as the anti-popoff polymer. Of course, by the term "effective amount," it refers to any amount of a suitable anti-popoff polymer in an ethylene polymer sheet material that can increase and substantially maintain tape adhesion between the ethylene polymer sheet material and a tape-tab fastener following initial and/or repeated re-fastenable use.

Figure 2:
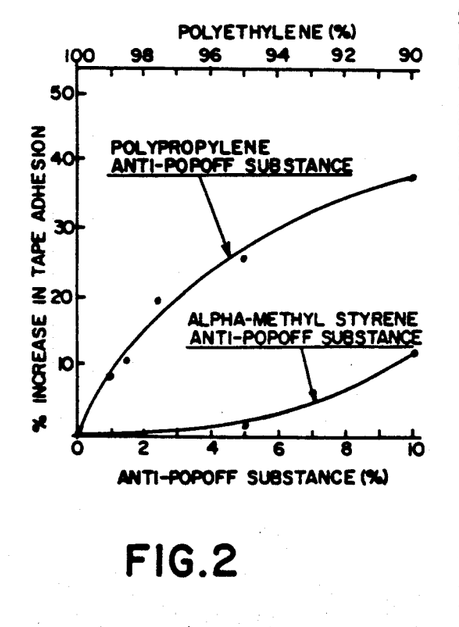
FIG. 2 is a graphic illustration exemplifying the percent increase in tape adhesion of a thermoplastic polyethylene sheet material formulated with a polypropylene or alpha-methyl styrene anti-popoff substance in accordance with the present invention.

Exemplary of two preferred formulations for producing a thermoplastic sheet material contemplated by the present invention comprises a polyethylene as the ethylene polymer and a polypropylene or alpha-methyl styrene as the anti-popoff polymer. Such formulations generally comprise by weight about 90 to about less than 100% polyethylene and about greater than 0 to about 10% polypropylene or alpha-methyl styrene. As reflected in FIG. 2, there is a dramatic increase in tape adhesion when polypropylene is selected as the anti-popoff polymer. There is, however, only a gradual increase in tape adhesion when alpha-methyl styrene is utilized as the anti-popoff polymer. This is also reflected in FIG. 2. Even when minor amounts of polypropylene are blended into the sheet materials, the tape adhesion still dramatically increases as compared to a similar thermoplastic polyethylene sheet material having no polypropylene incorporated therein. This can be observed in Table I (Test method A) and Table II (Test method B) where the polypropylene accounts for only about 0.75% and about 1.3% of the weight of the sheet materials, respectively.

TABLE I

| Percent Increase in Tape Adhesion (%) - Test Method A | | |
|---|---|---|
| Anti-popoff Polymer (polypropylene) Content (%) | Thermoplastic Polyethylene Sheet Material | |
| | 0 | 0.75 | 1.3 |
| Commercial Diaper Tape-Tab 1 | — | 6% | 11% |
| Commercial Diaper Tape-Tab 2 | — | 5% | 8% |

TABLE II

| Percent Increase in Tape Adhesion (%) - Test Method B | | |
|---|---|---|
| Anti-popoff Polymer substance (polypropylene) Content (%) | Thermoplastic Polyethylene Sheet Material | |
| | 0 | 0.75 | 1.3 |
| Commercial Diaper Tape-Tab 1 | — | 3% | 11% |
| Commercial Diaper Tape-Tab 2 | — | 2% | 12% |

As a further feature of the present invention, the tape adhesion between a sheet material having an anti-popoff polymer and a tape-tab fastener remains substantially the same even after a repeated number of refastenings. This feature is demonstrated in FIG. 4 wherein the percent increase in tape adhesion between a polyethylene backsheet containing 5% polypropylene and commercial tape-tab fastener 5 remained virtually the same as when compared to the tape adhesion between a similar polyethylene backsheet free of polypropylene and commercial tape-tab fastener 5 after five refastenings.

It should be appreciated, however, that eventhough the tape adhesion between a sheet material of this invention and a tape-tab fastener following a repeated number of fastenings might be less than the original fastening, it is nevertheless believed that such tape adhesion will usually be greater than the adhesion between a sheet material free of an anti-popoff polymer and a tape-tab fastener having an equal number of refastenings. Therefore, the term "substantially maintaining tape adhesion" is used herein in a broad sense to refer to not only those instances where the tape adhesion increases or remains substantially the same following repeated fastenings but also to those instances where there is any increase in tape adhesion between the sheet materials of the present invention and a tape-tab fastener over the tape adhesion between similar sheet materials free of anti-popoff polymer and a tape-tab fastener following refastening.

While the inventors do not wish to be limited to any particular theory in which the tape adhesion is increased and substantially maintained, they presently believe that the incorporation of a minor amount of an anti-popoff polymer into a thermoplastic ethylene-based sheet material interrupts the surface packing of the ethylene polymer, particularly when the ethylene polymer is a polyethylene, resulting in higher surface free-energy associated with the sheet material thus improving the adhesion of pressure-sensitive adhesive fasteners thereto. It is also presently believed that the objectives of this invention can be easily met particularly when the pressure-sensitive adhesive formulation of the selected tape-tab to be used is known by selecting an anti-popoff polymer that has a high bonding affinity for the particular pressure-sensitive adhesive. Even when the pressure-sensitive adhesive formulation is unknown, it is still believed that the objectives of this invention can be met by utilizing one of the polymeric substances employed to formulate the backsheet tab of the tape-tab fastener selected as the anti-popoff Polymer. Speaking, a polymeric substance commonly utilized to formulate the backsheet tabs of tape-tabs today particularly in the disposable diaper industry is a polypropylene. Since polypropylene generally has a high bonding affinity for the pressure-sensitive adhesives utilized with the tape-tab fasteners and is the commonly employed polyolefin utilized to form the backsheet tabs of the tape-tab fasteners, these factors make polypropylene a preferred anti-popoff polymer.

Basically any commercially available pressure-sensitive adhesive tape-tab fasteners used in disposable diaper construction today are suitable for use with the thermoplastic sheet materials of the present invention. For example, six different commercially available pressure-sensitive adhesive tape-tab fasteners have been utilized herein, and all six have been found to be substantially equally suitable. While the precise formulas of the pressure-sensitive adhesives utilized to form the six different tape-tab fasteners are unknown, it is presently believed that the pressure sensitive adhesive of tape-tab fastener 5 comprises a styrene-isoprene-styrene block copolymer base, an aliphatic mixed olefin tackifying resin and an anti-oxidant. It is also believed that the backsheet tab of tape-tab fastener 5 is formed with a polypropylene. Of course, it should also be appreciated that there are many other commercially available tape-tab fasteners being used by the disposable-diaper manufacturers that have pressure-sensitive adhesive formulations which are different than the pressure-sensitive adhesive formula of tape-tab fastener 5 described above that are also suitable for use with the present invention.

The commercial tape-tab fastener 5 referred to above can be easily prepared by any conventional means, such as by coating the pressure-sensitive adhesive composition just described onto the face side of a polypropylene-backing tab.

Figure 1:
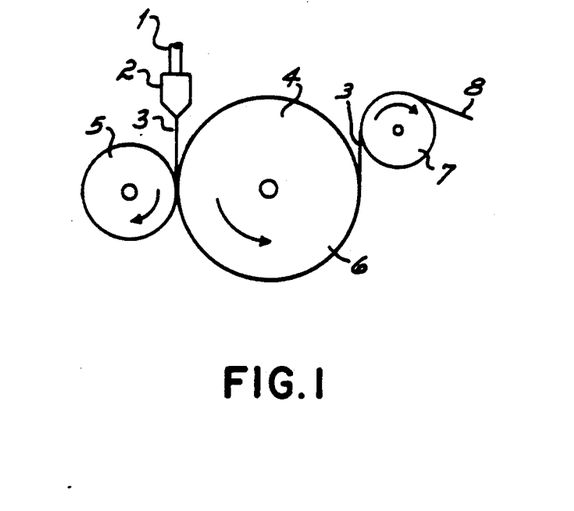
FIG. 1 is a diagrammatic view in side elevation of a schematic system of an extrusion apparatus suitable for producing the thermoplastic sheet materials of the present invention.

With reference now to FIG. 1, a slot cast film extrusion method for making the thermoplastic sheet materials of the present will be described. In this method, the thermoplastic sheet materials are generated simply by blending a selected ethylene polymer with a particular anti-popoff polymer in an effective amount and extruding the mixture through a conventional extrusion die adapter 1 and cast film die 2 to form the molten web 3. Molten web 3 is then rolled between a metal roll 4 and a rubber roll 5. When an embossed film is desired, an embossing section 6 is located on metal roll 4. The sheet materials can be embossed with any suitable design according to any of a number of well-known techniques. For example, embossing can be performed by the introduction of a pre-formed sheet material into a system of embossing rolls or by the introduction of an extruded melt of the thermoplastic material through a slot-die between embossing rolls. The molten web 3 is then directed onto a chilled metal roll 7 to form the cooled extruded film 8 which is then wound onto a storage roll (not shown). While the above describes thermoplastic sheet materials of the present invention being produced by a slot cast film extrusion method, the thermoplastic sheet materials can be produced by blown film extrusion methods as well. These different processes of making and embossing are described in more detail in U.S. Pat. Nos. 4,535,021, 4,546,029, 4,376,147 and 3,484,835 which are incorporated herein in their entirety by reference.

In a further feature of the present invention, the thermoplastic sheet materials can be produced by either single extrusion or co-extrusion. When the sheet materials are produced by single extrusion, the anti-popoff substance is generally dispersed throughout the single layer of the films. When the sheet materials are co-extruded, the anti-popoff polymer can be generally dispersed either throughout each layer or throughout one or more layers of the films. For instance, the anti-popoff Polymer can be generally dispersed throughout the top and/or bottom layers of a two layer or the top, bottom and/or middle layers of a three layer co-extruded film. It is necessary, however, to disperse the anti-popoff polymer at least throughout the layer of the co-extruded sheet material that is to receive the tape-tab fastener thereon.

Although the sheet materials can be formulated by adding the anti-popoff polymer directly to the ethylene polymer to form a pre-extrusion mixture, it is found that better results are achieved when the selected ethylene polymer is blended with a concentrate containing, inter alia, the anti-popoff polymer. The concentrate may also include, for instance, an ethylene polymer carrier, such as a conventional low density polyethylene or a conventional linear low density polyethylene, and titanium dioxide as a whitener. Preferred concentrates are those in which the anti-popoff Polymer is polypropylene wherein the polypropylene is present in an amount ranging from about 5 to about 50% by weight of the concentrate. Such preferred concentrates can further include the ethylene polymer carrier in an amount ranging from about 45% to about 0% and titanium dioxide (TiO$_2$) in an amount of about 50% by weight. Examples of three formulations of such preferred concentrates suitable for use in accordance with the teachings of the present invention are designated as Concentrates I-IV as follows:

| Concentrate | I | II | III | IV |
| --- | --- | --- | --- | --- |
| polypropylene parts | 5 | 25 | 45 | 50 |
| polyethylene parts | 45 | 25 | 5 | 0 |
| TiO$_2$ parts | 50 | 50 | 50 | 50 |
| Total Parts | 100 | 100 | 100 | 100 |

The preferred concentrate should be intimately blended with an ethylene polymer and in particular a polyethylene in an amount ranging from about 8 to about 10 parts concentrate to about 100 parts polyethylene to form the pre-extrusion mixture which can then be extruded as described above to form liquid-pervious or liquid-impervious sheet materials, such as backsheets.

The thermoplastic sheet materials of the present invention are especially suitable for use with absorbent articles, such as disposable diapers, bandages, surgical dressings or drapes and catamenial pads and most particularly with disposable diapers. When the thermoplastic sheet materials are to be used with the absorbent articles, they can be formulated into thin films that are either liquid-pervious or liquid-impervious, that have either smooth or embossed surfaces and that have either dull or glossy finishes. The thickness of the film can vary over a wide range. When the thermoplastic sheet materials are to be formulated into thin films that are to be used as backsheets for absorbent articles, it is preferred, but not necessary, that the thin films are moisture-impervious having embossed surfaces and dull finishes. Typically, such thin backsheet films can have a thickness ranging from about 0.5 mils to about 2.0 mils and preferably about 1.0 mils to about 1.5 mils, but these limitations are not critical. Of course, when selecting a film thickness, the tearing strength of the film should not be overlooked so that the objectives of the present invention are not defeated.

A typical disposable diaper practicing the objectives of the present invention generally includes a moisture-pervious inner frontsheet, an outer backsheet of the present invention which is preferably moisture-impervious, an absorbent material or layer positioned between the outer backsheet and inner frontsheet and tape-tab fasteners secured to the disposable diaper. The moisture-pervious inner frontsheet forms the diaper inside surface for direction toward an infant and the outer backsheet forms a diaper outside surface for direction away from the infant when the disposable diaper is worn by the infant. To secure the tape-tab fasteners to the disposable diaper, the tape-tab fasteners generally speaking have anchoring ends which are secured to the disposable diaper and user ends which have on one side thereof a pressure-sensitive adhesive presenting tacky surfaces facing in the same direction as the diaper inside surface for contact with the backsheet when the diaper is fitted about an infant. Other absorbent articles such as bandages, surgical dressings or drapes and catamenial pads, on the other hand, generally comprise the same three elements as the disposable diaper absent the tape-tab fasteners. As an additional benefit, the anti-popoff technology improves the ability to assemble the components of such absorbent products together, such as the glue, backsheets, etc.

Examples of the increase in tape adhesion between a thermoplastic sheet material of the present invention will now be further illustrated with reference to the following examples.

EXAMPLE I

A polyethylene in combination with anti-popoff substances are extruded to form the thermoplastic backsheets having increased tape adhesion for preventing the disposable diaper tape-tab fasteners from popping off the backsheets. For instance, about 5% of a conventional polypropylene and about 95% of a conventional polyethylene can be blended and extruded into thin films in the range of about 1.0 to about 1.5 mils which can then be used as backsheets. As indicated in Tables III and IV, the tape adhesion dramatically increases with a thermoplastic sheet material having about 5% polypropylene incorporated therein as when compared to a similar thermoplastic sheet material without polypropylene. It is also believed that any conventional polypropylene, such as shown in Tables I and II, will have the same effect on increasing the tape adhesion.

More precisely, the amount of anti-popoff Polymer needed to increase tape adhesion depends of course upon the interaction of the pressure-sensitive adhesive of the tape-tab fasteners and the film. Another example of an increase in tape adhesion attributed to the use of an anti-popoff polymer is described in Example II.

TABLE III

|  | Film Comprising 100% PE by weight | Film Comprising 95% PE and 5% PP - 1 by weight | Film Comprising 95% PE and 5% PP - 2 by weight |
|---|---|---|---|
| Percent (%) increase in tape adhesion by using Method B | 0 | 26% | 21% |
| Percent (%) increase in tape adhesion by using Method C | 0 | 29% | 30% |

Commercial tape-tab fastener 5
PE - conventional polyethylene
PP - 1 - a conventional polypropylene
PP - 2 - another conventional polypropylene

TABLE IV

|  | Film Comprising 100% PE by weight | Film Comprising 95% PE and 5% PP - 1 by weight | Film Comprising 95% PE and 5% PP - 2 by weight |
|---|---|---|---|
| Percent (%) increase in tape adhesion by using Method B | 0 | 25% | 16% |
| Percent (%) increase in tape adhesion by using Method C | 0 | 25% | 13% |

Commercial tape-tab fastener
PE - conventional polyethylene
PP - 1 - a conventional polypropylene
PP - 2 - another conventional polypropylene

EXAMPLE II

The thermoplastic sheet materials and tape adhesions referred to in Tables I and II are prepared and determined as follows.

A first concentrate is prepared which comprises 40 parts of a conventional thermoplastic low density polyethylene, 10 parts of a conventional thermoplastic polypropylene and 50 parts titanium dioxide. Eight parts of the prepared concentrate are intimately blended with 100 parts of a conventional polyethylene to form a first pre-extrusion mixture. The first pre-extrusion mixture is then extruded in accordance with the extrusion equipment and procedures described herein to generate a first thin thermoplastic film which comprises by weight about 0.75% polypropylene, about 3.70% titanium dioxide and about 95.55% polyethylene. The first extruded film has a thickness of about 1.5 mils, an embossed surface, a dull finish and is moisture-impervious.

A second concentrate is prepared which comprises 35 parts of a conventional thermoplastic low density polyethylene, 15 parts of a conventional thermoplastic polypropylene and 50 parts titanium dioxide. Nine parts of the prepared concentrate are intimately blended with 100 parts of a conventional polyethylene to form a second pre-extrusion mixture. The second pre-extrusion mixture is then extruded in accordance with the extrusion equipment and procedures described herein to generate a second, thin thermoplastic film which comprises by weight about 1.3% polypropylene, 4.1% titanium dioxide and 94.6% polyethylene. The second extruded film has a thickness of about 1.5 mils, an embossed surface and a dull finish and is moisture-impervious.

Figure 3:
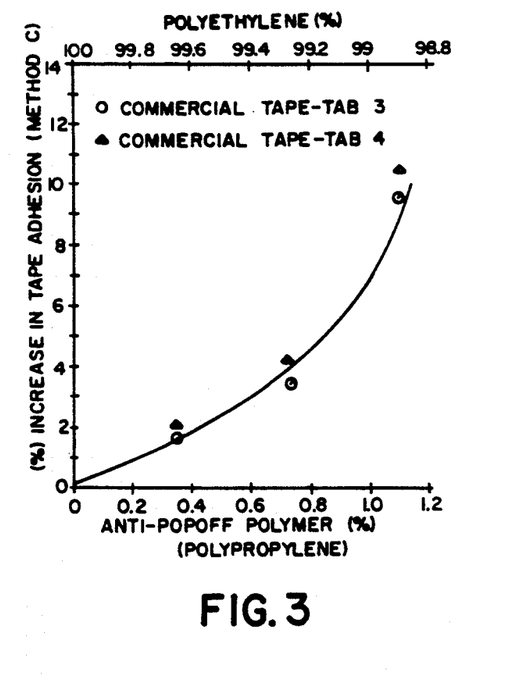
FIG. 3 is a graphic illustration exemplifying the percent increase in tape adhesion of two different commercially available tape-tab fasteners when they are separated (Method C) from a thermoplastic polyethylene sheet material formulated with various concentrations of a polypropylene anti-popoff substance in accordance with the present invention.

As indicated in Tables I and II, the tape adhesion for the first and second films when bonded with commercial diaper tape-tab fasteners 1 and 2 is expressed in percent (%) increase in tape adhesion of a polyethyelene film containing a polypropylene over a similar polyethylene film free of a polypropylene. The 90° (Method A) and 180° (Method B) tape adhesions are determined as follows. Two 5-inch length and 1-inch width specimens of each commercial diaper tape-tab are applied to each film. Approximately 1 inch at the end of each tape-tab specimen is left free (unbonded). A roller is passed over each applied specimen once in a lengthwise direction. Care is exercised to ensure that no air bubbles are entrapped. Following adhesion, the tests are conducted immediately. For determining the 90° (Method A) and 180° (Method B) tape adhesions, the free end of each specimen is double backed at an angle of 90° (Method A) or 180° (Method B) and 1 inch of the secured end of each tape-tab specimen is peeled from the film. The peeled end of the tape-tab specimen is then clamped into the lower jaw of the adhesion testing machine manufactured by Instron Corporation and the free end of the tape-tab specimen is changed into the upper jaw. The lower jaw of the testing machine is operated at 12 inches per minute. After the lower jaw is started in motion, the values obtained for the first inch of the tape-tab specimens are disregarded. The average pull value obtained during the peeling of the next 2 inches is used and recorded as the percent increase in tape adhesion of the tape-tab specimens. The above as well as other suitable test procedures are described in the manual entitled "Test Methods for Pressure Sensitive Tapes", 7th ed., copyright 1976, published by the Pressure Sensitive Tape Council which is incorporated herein in its entirety by reference. In addition to the 90° (Method A) and 180° (Method B) angle test procedures for determining tape adhesion, there are other tests to develop the tape adhesion. For example, as already indicated herein and illustrated in FIG. 3 and Tables III and IV, the tape adhesion can be determined at angles between 90° and 180° (Method C). Two different commerically available tape-tab fasteners are used in this example.

EXAMPLE III

The percent increase in tape adhesion betwen a polyethylene backsheet containing 5% polypropylene and a tape-tab fastener 5 described herein over the tape adhesion between a similar polyethylene backsheet but containing no polypropylene and a similar tape-tab fastener 5 is determined following an original fastening and four repeated refastenings of the tape-tab fastener 5 to the backsheets. The polyethylene backsheets containing polypropylene are similar to those described and referred to in Example I and Tables III and IV. Under Methods B and C as described herein and referred to in FIG. 4, the tape adhesion is determined. Similar backsheets and tape-tab fasteners 5 are used for both Methods B and C.

Figure 4:
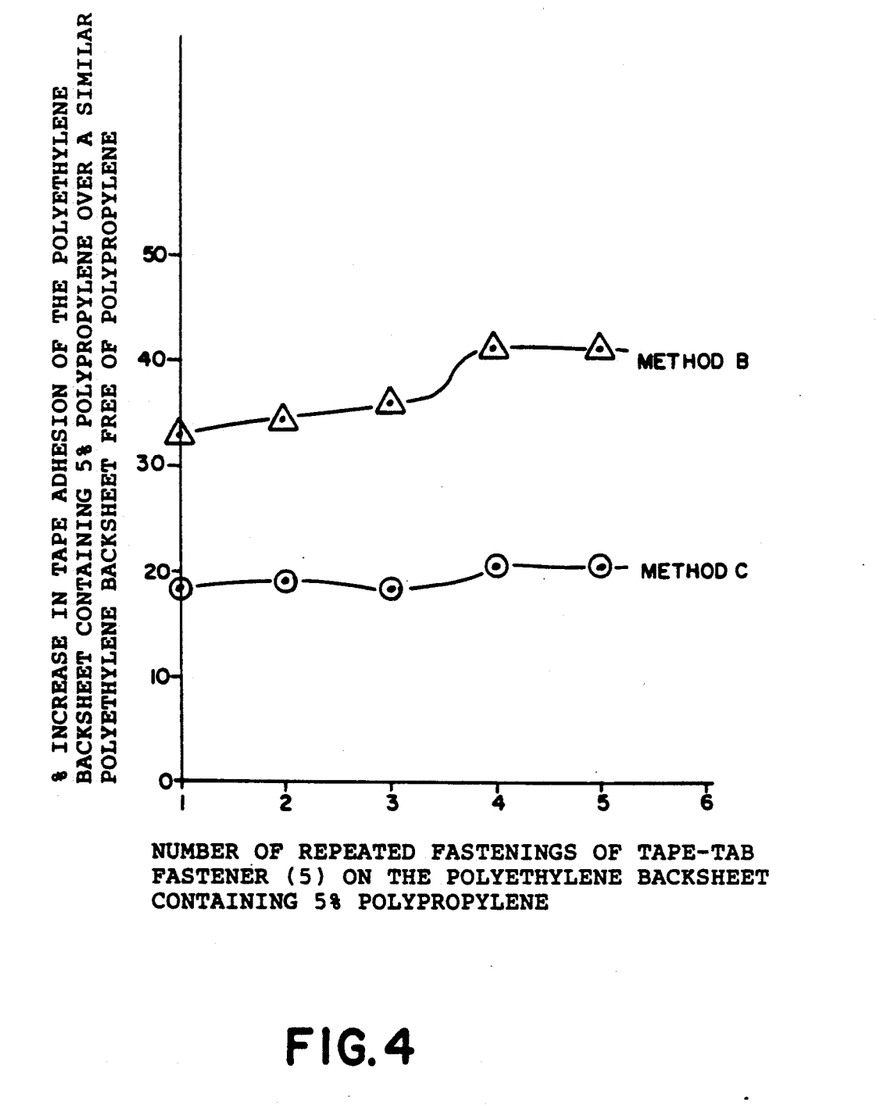
FIG. 4 is a graphic illustration comparing the percent increase in tape adhesion between a polyethylene backsheet containing 5% polypropylene and a commercial tape-tab fastener designated herein as tape-tab fastener 5 over the tape adhesion between a similar polyethylene backsheet free of polypropylene and a similar commercial tape-tab fastener 5 following an initial fastening and four refastenings.

Under Method B, FIG. 4 reports that there is approximately a 33% increase in tape adhesion following the original fastening between a polyethylene backsheet containing 5% polypropylene and the tape-tab fastener 5 over the tape adhesion between a polyethylene backsheet free of polypropylene and a similar tape-tab fastener 5. FIG. 4 also demonstrates that there is a further increase in tape adhesion between the polyethylene backsheet containing 5% polypropylene and the tape-tab fastener 5 over the polyethylene backsheet free of polypropylene and the tape-tab fastener 5 following four repeated refastenings.

Under Method C, FIG. 4 reports that there is approximately a 19% increase in tape adhesion following the original fastening between a polyethylene backsheet containing 5% polypropylene and the tape-tab fastener 5 over the tape adhesion between a polyethylene backsheet free of polypropylene and a similar tape-tab fastener 5. FIG. 4 also demonstrates that the percent increase in tape adhesion between the polyethylene backsheet containing 5% polypropylene and the tape-tab fastener 5 is substantially maintained over the tape adhesion between the polyethylene backsheet free of polypropylene and the tape-tab fastener 5 following four repeated refastenings.

The present invention may, of course, be carried out in other specific ways than those herein set forth without departing from the spirit and essential characteristics of the present invention. The present embodiments are, therefore, to be considered in all respects as illustrative and not restrictive and any changes coming within the meaning and equivalency range of the appended claims are to be embraced therein.

What is claimed is.

1. A disposable diaper having an improved backsheet for increasing and substantially maintaining tape adhesion between a tape-tab fastener and the backsheet for permitting the tape-tab fastener to be positioned and repeated repositioned thereon, said disposable diaper comprises:
   a liquid-pervious frontsheet which forms a diaper inside surface for direction toward an infant when the disposable diaper is worn by the infant;
   a tape-tab fastener having an anchoring end and an user end, the anchoring end being secured to said disposable diaper and the user end having on one side thereof a pressure-sensitive adhesive presenting a tacky surface facing in the same direction as the diaper inside surface;
   a backsheet which forms a diaper outside surface for direction away from the infant when the disposable diaper is worn by the infant, said backsheet comprises a blend of an ethylene polymer and an anti-popoff polymer, said anti-popoff polymer being selected from a group consisting of an ethylene-propylene copolymer, an alpha-methyl styrene, a styrene-butadiene-styrene block copolymer and a styrene-butadiene-styrene block copolymer and being present in said backsheet in an effective amount for increasing and substantially maintaining the tape adhesion between said backsheet and said tape-tab fastener when the tacky surface of the user end of said tape-tab fastener is positioned on said backsheet and adhered thereto via the pressure-sensitive adhesive for permitting said tape-tab fastener to be positioned and repeatedly positioned thereon, said backsheet having a tearing strength which is greater than the tape adhesion between said backsheet and said tape-tab fastener; and
   an absorbent layer positioned between said backsheet and said frontsheet.

2. A disposable diaper of claim 1 wherein said anti-popoff polymer is present in said backsheet in an amount of from about greater than zero up to about ten percent.

3. A disposable diaper of claim 1 wherein said backsheet is liquid-impervious.

4. A disposable diaper of claim 1 wherein said ethylene polymer is a homopolymer or a copolymer of ethylene.

5. A disposable diaper of claim 1 wherein said ethylene polymer is a polyethylene.

6. A disposable diaper of claim 1 wherein said backsheet further includes titanium dioxide.

7. An improved thermoplastic sheet material for increasing and substantially maintaining tape adhesion between a tape fastener and said thermoplastic sheet material for permitting the tape fastener to be positioned and repeatedly repositioned thereon, said thermoplastic sheet material comprises a blend of:
   an ethylene polymer; and
   an anti-popoff polymer selected from a group consisting of an ethylene-propylene copolymer, an alpha-methyl styrene, a styrene-butadiene-styrene block copolymer and a styrene-isoprene-styrene block copolymer and being present in an effective amount for increasing and substantially maintaining tape adhesion between said thermoplastic sheet material and a tape fastener having on one side thereof a pressure-sensitive adhesive for permitting the tape fastener to be positioned and repeatedly repositioned thereon following the original attachment of the tape fastener to said thermoplastic sheet material via the pressure-sensitive adhesive, said thermoplastic sheet material having a tearing strength which is greater than the tape adhesion between said thermoplastic sheet material and the tape fastener.

8. A thermoplastic sheet material of claim 7 wherein said anti-popoff polymer is present in said thermoplastic sheet material in an amount by weight of from about greater than zero up to about ten percent.

9. A thermoplastic sheet material of claim 7 wherein said thermoplastic sheet material is liquid-impervious.

10. A thermoplastic sheet material of claim 7 wherein said ethylene polymer is a homopolymer or a copolymer of ethylene.

11. A thermoplastic sheet material of claim 7 wherein said ethylene polymer is a polyethylene.

12. A thermoplastic sheet material of claim 7 wherein said thermoplastic sheet material further includes titanium dioxide.

13. An absorbent article having an improved backsheet for increasing and substantially maintaining tape adhesion between a tape fastener and the backsheet for permitting a tape fastener to be positioned and repeatedly repositioned thereon, said absorbent article comprises:
   a liquid-pervious frontsheet which forms and article inside surface for direction toward a person when the absorbent article is worn by the person;
   a backsheet which forms an article outside surface for direction away from the person when the absorbent article is worn by the person, said backsheet comprises a blend of an ethylene polymer and an anti-popoff polymer, said anti-popoff polymer being selected from a group consisting of a polypropylene, an ethylene-propylene copolymer, an alpha-methyl styrene, a styrene-butadiene-styrene block copolymer and a styrene-isoprene-styrene block copolymer and being present in said backsheet in an effective amount for increasing and substantially maintaining tape adhesion between said backsheet and a tape fastener having on one side thereof a pressure-sensitive adhesive for permitting the tape fastener to be positioned and repeatedly repositioned thereon following the original attachment of the tape fastener to said backsheet via the pressure-sensitive adhesive, said backsheet having a tearing strength which is greater than the tape adhesion between said backsheet and the tape fastener; and
   an absorbent layer positioned between said backsheet and said frontsheet.

14. An absorbent article of claim 13 wherein said absorbent article is selected from a group consisting of a disposable diaper, a bandage, a surgical dressing, a surgical drape and a catamenial pad.

15. An absorbent article of claim 13 wherein said anti-popoff polymer is present in said backing sheet in an amount by weight from about greater than zero to about ten percent.

16. An absorbent article of claim 13 wherein said backsheet is liquid-impervious.

17. An absorbent article of claim 13 wherein said ethylene polymer is a homopolymer or a copolymer of ethylene.

18. An absorbent article of claim 13 wherein said ethylene polymer is a polyethylene.

19. An absorbent article of claim 13 wherein said backsheet further includes titanium dioxide.

20. A thermoplastic sheet material of claim 7 which is produced by the process which comprises the step of extruding a mixture comprising the ethylene polymer and a concentrate containing the anti-popoff polymer to form the thermoplastic sheet material.

21. A thermoplastic sheet material of claim 20 wherein the ethylene polymer is a homopolymer or a copolymer.

22. A thermoplastic sheet material of claim 20 wherein the ethylene polymer is a polyethylene.

23. A thermoplastic sheet material of claim 20 wherein said anti-popoff polymer is present in the concentrate in an amount ranging from about 5 to about 50 percent by volume.

24. A thermoplastic sheet material of claim 20 wherein the concentrate further contains an ethylene polymer carrier.

25. A thermoplastic sheet material of claim 20 wherein the concentrate contains said anti-popoff polymer in an amount ranging from about 5 to about 50%, an ethylene polymer carrier in an amount ranging from 0 to about 45 percent and titanium dioxide in an amount of up to about 50 percent by weight.

26. A thermoplastic sheet material of claim 25 wherein the mixture comprises the ethylene polymer in an amount ranging from about 100 parts and the concentrate in an amount ranging from about 8 to about 10 parts.

27. A thermoplastic sheet material of claim 20 wherein the process further comprises the step of preparing the mixture prior to said extruding.

28. A thermoplastic sheet material of claim 7 which is produced by the process which comprises the step of extruding a mixture comprising the ethylene polymer and the anti-popoff polymer to form the thermoplastic sheet material.

29. A thermoplastic sheet material of claim 28 wherein the process further comprises the step of preparing the mixture prior to said extruding.

30. A thermoplastic sheet material of claim 28 wherein the mixture comprises the ethylene polymer in an amount ranging from about 90 parts up to less than about 100 parts and the anti-popoff polymer in an amount ranging from greater than about zero parts up to about 10 parts.

31. A thermoplastic sheet material of claim 28 wherein the ethylene polymer is a polyethylene.

32. A disposable diaper of claim 1 wherein said backsheet is a co-extruded backsheet having more than one layer and said anti-popoff polymer is dispersed at least throughout the layer which is to receive said tape-tab fastener thereon.

33. A thermoplastic sheet material of claim 7 wherein said thermoplastic sheet material is a co-extruded thermoplastic sheet material having more than one layer and said anti-popoff polymer is dispersed at least throughout the layer which is to receive a tape fastener thereon.

34. An absorbent article of claim 13 wherein said backsheet is a co-extruded backsheet having more than one layer and said anti-popoff polymer is dispersed at least throughout the layer which is to receive a tape fastener thereon.

35. A disposable diaper having an improved backsheet for increasing and substantially maintaining tape adhesion between a tape-tab fastener and the backsheet for permitting the tape-tab fastener and the backsheet for permitting the tape-tab fastener to be positioned and repeatedly repositioned thereon, said disposable diaper comprises:
   a liquid-pervious frontsheet which forms a diaper inside surface for direction toward an infant when the disposable diaper is worn by the infant;

a tape-tab fastener having an anchoring end and an user end, the anchoring end being secured to said disposable diaper and the user end having on one side thereof a pressure-sensitive adhesive preventing a tacky surface facing in the same direction as the diaper inside surface;

a backsheet which forms a diaper outside surface for direction away from the infant when the disposable diaper is worn by the infant, said backsheet comprises a blend of an ethylene polymer and an anti-popoff propylene polymer, said anti-popoff propylene polymer being present in said backsheet in an effective amount for increasing and substantially maintaining the tape adhesion between said backsheet and said tape-tab fastener when the tacky surface of the user end of said tape-tab fastener is positioned on said backsheet and adhered thereto via the pressure-sensitive adhesive for permitting said tape-tab fastener to be positioned and repeatedly repositioned thereon; and an absorbent layer positioned between said backsheet and said frontsheet.

36. A disposable diaper of claim 35 wherein said ethylene polymer is a polyethylene.

37. An absorbent article having an improved backsheet for increasing and substantially maintaining tape adhesion between a tape fastener and the backsheet for permitting a tape fastener to be positioned and repeatedly repositioned thereon, said absorbent article comprises:

a liquid-pervious frontsheet which forms and article inside surface for direction toward a person when the absorbent article is worn by the person;

a backsheet which forms an article outside surface for direction away from the person when the absorbent article is worn by the person, said backsheet comprises a blend of an ethylene polymer and an anti-popoff polymer, said anti-popoff polymer being present in said backsheet in an effective amount for increasing and substantially maintaining tape adhesion between said backsheet and a tape fastener having on one side thereof a pressure-sensitive adhesive for permitting the tape fastener to be positioned and repeatedly repositioned thereon following the original attachment of the tape fastener to said backsheet via the pressure-sensitive adhesive; and an absorbent layer positioned between said backsheet and said frontsheet.

38. An absorbent article of claim 37 wherein the said ethylene polymer is a polyethylene.

39. An improved thermoplastic sheet material for increasing and substantially maintaining tape adhesion between a tape fastener and said thermoplastic sheet material for permitting the tape fastener to be positioned and repeatedly repositioned thereon, said thermoplastic sheet material being produced by the process which comprises the step of:

extruding a mixture comprising an ethylene polymer and a concentrate containing an anti-popoff polymer selected from a group of anti-popoff polymers consisting of an ethylene-propylene copolymer, an alpha-methylstyrene polymer, a styrene-butadiene-styrene block copolymer and a styrene-isoprene-styrene block copolymer to form the thermoplastic sheet material, said anti-popoff polymer being present in the concentrate in an effective amount for increasing and substantially maintaining tape adhesion between said thermoplastic sheet materials and a tape fastener having on one side thereof a pressure-sensitive adhesive for permitting the tape fastener to be positioned and repeatedly repositioned thereon following the original attachment of the tape fastener to said thermoplastic sheet material via the pressure-sensitive adhesive.

40. An improved thermoplastic sheet material of claim 39 wherein the ethylene polymer is a polyethylene.

41. A disposable diaper of claim 35 wherein said anti-popoff propylene polymer is polypropylene.

42. A disposable diaper of claim 35 wherein said anti-popoff propylene polymer is present in said backsheet in an amount by weight of from about greater than zero up to about ten percent.

43. A disposable diaper of claim 35 wherein said backsheet is liquid-impervious.

44. A disposable diaper of claim 35 wherein said ethylene polymer is a homopolymer or a copolymer of ethylene.

45. A disposable diaper of claim 35 wherein said backsheet further includes titanium dioxide.

46. A disposable diaper of claim 41 wherein said polypropylene is present in said backsheet in an amount between about 0.75% and about 5.0% by weight.

47. An absorbent article of claim 37 wherein said propylene polymer is polypropylene.

48. An absorbent article of claim 37 wherein said anti-popoff polymer is present in said backsheet in an amount by weight of from about greater than zero up to about 10%.

49. An absorbent article of claim 37 wherein said backsheet is liquid-impervious.

50. An absorbent article of claim 37 wherein said ethylene polymer is a homopolymer or a copolymer of ethylene.

51. An absorbent article of claim 37 wherein said backsheet further includes titanium dioxide.

52. An absorbent article of claim 47 wherein said polypropylene is present in said backsheet in an amount between about 0.75% and about 5.0% by weight.

53. A disposable diaper as recited in claim 35, said backsheet having a thickness of about 1.5 mils, said backsheet comprising by weight about 0.75% polypropylene, about 3.7% titanium dioxide and about 95.55% polyethylene.

54. A disposable diaper as recited in claim 53, said backsheet further having an embossed surface and a dull finish and being moisture-impervious.

55. A disposable diaper of claim 35, said backsheet having a thickness of about 1.5 mils and comprising by weight about 1.3% polypropylene, about 4.1% titanium dioxide and about 94.6% polyethylene.

56. A disposable diaper as recited in claim 55, said backsheet further having an embossed surface and a dull finish and being moisture-impervious.

57. A disposable diaper of claim 35, said backsheet comprising by weight about 95% polyethylene and about 5% polypropylene.

58. An absorbent article as recited in claim 37, said backsheet having a thickness of about 1.5 mils, said backsheet comprising by weight about 0.75% polypropylene, about 3.7% titanium dioxide and about 95.55% polyethylene.

59. An absorbent article as recited in claim 58, said backsheet further having an embossed surface and a dull finish and being moisture-impervious.

60. An absorbent article of claim 37, said backsheet having a thickness of about 1.5 mils and comprising by weight about 1.3% polypropylene, about 4.1% titanium dioxide and about 94.6% polyethylene.

61. An absorbent article as recited in claim 60, said backsheet further having an embossed surface and a dull finish and being moisture-impervious.

62. An absorbent article of claim 37, said backsheet comprising by weight about 95% polyethylene and about 5% polypropylene.

* * * * *

UNITED STATES PATENT AND TRADEMARK OFFICE
CERTIFICATE OF CORRECTION

PATENT NO. : 5,084,039

DATED : January 28, 1992

INVENTOR(S) : Leopoldo V. Cancio et al

It is certified that error appears in the above-identified patent and that said Letters Patent is hereby corrected as shown below:

Column 12, line 15, "styrene-butadiene-styrene" should be --styrene-isoprene-styrene--

Signed and Sealed this

Second Day of November, 1993

Attest:

BRUCE LEHMAN

*Attesting Officer*    *Commissioner of Patents and Trademarks*